United States Patent
Massen et al.

(10) Patent No.: US 7,852,493 B2
(45) Date of Patent: Dec. 14, 2010

(54) OPTICAL RECORDING OF THE SPATIAL SHAPE OF BODIES AND BODY PARTS WITH SECTIONS THAT IN PART ARE NOT OPTICALLY VISIBLE

(75) Inventors: Robert Massen, Oehingen-Wangen (DE); Dirk Rutschmann, Stuttgart (DE); Holger Reinhardt, Kempen (DE)

(73) Assignee: corpus.e AG, Stuttgart (DE)

( * ) Notice: Subject to any disclaimer, the term of this patent is extended or adjusted under 35 U.S.C. 154(b) by 901 days.

(21) Appl. No.: 10/589,271

(22) PCT Filed: Feb. 3, 2005

(86) PCT No.: PCT/EP2005/001089

§ 371 (c)(1),
(2), (4) Date: Apr. 26, 2007

(87) PCT Pub. No.: WO2005/077271

PCT Pub. Date: Aug. 25, 2005

(65) Prior Publication Data
US 2007/0288198 A1    Dec. 13, 2007

(30) Foreign Application Priority Data
Feb. 13, 2004  (DE) .................. 10 2004 007 455

(51) Int. Cl.
*G01B 11/14* (2006.01)
*G06K 9/00* (2006.01)

(52) U.S. Cl. .................. 356/625; 356/601; 382/154; 382/128

(58) Field of Classification Search .................. 356/601, 356/603, 608, 614, 616, 622, 627, 5.15, 4.01; 250/559.2, 559.21, 559.22, 559.29, 561, 250/558, 334; 382/154, 103, 106, 284, 286
See application file for complete search history.

(56) References Cited

U.S. PATENT DOCUMENTS

| | | | |
|---|---|---|---|
| 4,974,331 A | | 12/1990 | Watterson et al. |
| 5,237,998 A | | 8/1993 | Duret et al. |
| 5,320,462 A | | 6/1994 | Johansson et al. |
| 5,457,325 A | * | 10/1995 | Huberty .................. 250/559.29 |
| 5,604,817 A | * | 2/1997 | Massen et al. .............. 382/120 |

(Continued)

FOREIGN PATENT DOCUMENTS

DE    38 07 578    9/1989

(Continued)

*Primary Examiner*—Sang Nguyen
(74) *Attorney, Agent, or Firm*—Stuart J. Friedman

(57) ABSTRACT

There is described a method and an apparatus for the optical 3D digitization of bodies and body parts which reveal non-visible regions which therefore cannot be detected by the 3D digitizer. A mechanical aid is fixed at these regions and protrudes into the measurement space visible for the 3D digitizer. On this visible part, it is provided with marks and is digitized together with the remaining, visible body parts. From the spatial position of the marks of these aids, important geometrical information of the non-visible parts, such as the spatial position, circumferential dimensions, etc., can be calculated, and the 3D model of the body or body part incomplete at these points can be completed therewith. Two applications from the field of orthopedics are described by way of example.

11 Claims, 2 Drawing Sheets

U.S. PATENT DOCUMENTS

| | | | |
|---|---|---|---|
| 5,800,364 A * | 9/1998 | Glennie et al. | 600/592 |
| 6,383,148 B1 * | 5/2002 | Pusch et al. | 600/587 |
| 6,549,289 B1 * | 4/2003 | Ellis | 356/603 |
| 6,993,179 B1 * | 1/2006 | Weinshall et al. | 382/154 |
| 7,095,886 B2 * | 8/2006 | Massen | 382/154 |
| 7,209,586 B2 * | 4/2007 | Massen | 382/154 |
| 7,298,889 B2 * | 11/2007 | Massen | 382/154 |
| 7,446,884 B2 * | 11/2008 | Massen | 356/601 |
| 2007/0055537 A1 | 3/2007 | Bassez et al. | |

FOREIGN PATENT DOCUMENTS

| | | |
|---|---|---|
| DE | 199 16 978 | 4/2001 |
| FR | 2 852 421 | 9/2004 |

* cited by examiner

OPTICAL RECORDING OF THE SPATIAL SHAPE OF BODIES AND BODY PARTS WITH SECTIONS THAT IN PART ARE NOT OPTICALLY VISIBLE

This invention relates to a method for the optical detection of the spatial shape of bodies and body parts with in part non-visible regions, and to an arrangement for performing this method.

The optical detection of the three-dimensional shape of bodies and body parts by means of so-called 3D scanners develops into an important technology in the production of products fitted to the human body, such as clothing, footwear, sports supports, orthopaedic and medicinal aids and the like. Due to the availability of very inexpensive methods based on the combination of image processing and photogrammetry, this technique is of interest in particular for orthopaedic applications. In EP 0 760 622 of the inventor Robert Massen, the general method of a particularly inexpensive 3D scanner is described, in which the body part to be digitized is provided with an elastic cover that carries marks to be evaluated by photogrammetry. By means of one or more only roughly positioned cameras, overlapping images are taken, and from the combination of these 2D images a 3D model of the body part is generated automatically. Under the designation "3D Image", this method has already been used by the firm Bauerfeind-Phlebologie AG, Zeulenroda, for producing fitted compression stockings (www.bauerfeind-phlebologie.de)

As with all optical 3D scanners, this method also has the restriction that only those parts of a body can be digitized, which can be detected by the cameras in the form of an image. In photogrammetric methods, all body parts to be digitized must even be detected as an image from at least two views, in order to be able to calculate the 3D model from the 2D images. The non-visible body regions are missing in the 3D model.

These missing regions represent a strong restriction for instance in the production of above-knee prostheses. The shaft to be fitted encloses the entire thigh, and in particular in the vicinity of the ramus (pelvic bone in the perineal region) it must have a firm physical contact precisely aligned in its angular position with respect to the ramus bone. This region is, however, optically non-visible. In the traditional method of the plaster cast, it is palpated manually by the orthopaedist, in order to transfer the spatial position and the spatial shape of the ramus to the gypsum die. These manually detected data are not available in numerical form and hence are very difficult to include into an automatically generated partial 3D model. Thus, the automatic detection of the spatial shape of the entire thigh for producing particularly well fitting prosthesis shafts only is possible to a restricted extent.

Another application not satisfactorily solved in the currently used optical 3D scanners is the determination of the spatial shape for the dimensionally accurate manufacture or size selection of compression stockings for obese patients, in which the region between the thighs is not visible for cameras. In this case, the required accurate circumferential dimensions are missing at these points. In the optically completely detected lower leg region, however, the circumferential dimensions can be determined with high accuracy from the 3D model (which here is complete). A pure extrapolation in the non-visible region of the thigh is inaccurate, as the cross-section does not reveal a simple circular or elliptical shape.

Therefore, a great economic interest exists in creating a method and an apparatus which during the optical 3D scanning of body parts does not omit the body parts non-visible for the optical systems in the generated 3D model, but for this purpose at least generates partial spatial information simultaneously with the complete spatial information of the body parts visible for the 3D scanner.

In accordance with the invention, this is achieved in that for the optical detection of the spatial shape of bodies and body parts by means of at least one 3D digitizer, at least one shape-retaining measurement aid is positively mounted to the body regions not visible for and not measurable by the at least one 3D digitizer such that the same protrudes into the measurement space visible for the at least one optical 3D digitizer, wherein at least at some points of its parts located in the visible measurement space this at least one measurement aid is provided with marks to be evaluated by the at least one 3D digitizer, and wherein these marks are located in a known spatial position with respect to the remaining parts of the measurement aid. The spatial position and the marks of this part of the measurement aid visible for the at least one 3D digitizer are determined together with the spatial shape of the remaining, visible body regions. From the measured spatial position of the visible part of the at least one measurement aid, geometric information such as height, angle, circumference, curvature and the like of the non-visible body part(s) is determined, and this information is used at these points for the supplementary description of the spatial shape digitized incompletely because of the non-visible regions.

The invention also relates to an arrangement for performing the method. This arrangement comprises a body or a body part with partly non-visible regions, and a rigid measurement aid with marks to be evaluated photogrammetrically, which is positively mounted on at least one of the non-visible regions of the body/body part (10). An optical 3D digitizer detects the spatial shape of the visible body regions and at least one visible part of the measurement aid and provides spatial coordinates to a computer, which spatial coordinates are determined by the 3D digitizer from the visible regions of the body or body part as well as from the visible part of the measurement aid. From the stored spatial shape of the measurement aid, the known position of the marks of the measurement aid with respect to the part of the measurement aid fixed to the non-visible body part, and from the spatial position of the visible part of the digitized body or body part, the computer determines geometrical information concerning the height, angle, circumference, curvature and the like of the non-visible body regions and uses this geometrical information for completing the spatial shape digitized incompletely because of the non-visible regions.

Advantageous embodiments of the method are included in the sub-claims.

This inventive idea will now be described by way of example, but not in a limiting way, with reference to two applications from the field of orthopaedics:

a) determination of spatial information from the (non-visible) region of the ramus near to the perineum during the 3D scanning of a thigh for producing a fitting shaft for an above-knee prosthesis b) determination of the circumference of the (not completely visible) thigh of obese patients for producing fitted compression stockings and compression tights The following Figures are used for illustration:

Traditionally, the patent requiring an above-knee prosthesis is cared for such that a plaster cast is taken manually from the thigh. In doing so, the skilled orthopaedist manually presses the still soft gypsum into the proper position in the area of the ramus, corresponding to the individual local anatomy of the male or female patient.

For the case of the automatic 3D digitization of the above-knee stump, we would like to describe the inventive idea by means of the example of the 3D digitization by means of a 3D technology in accordance with the above EP 0 760 622. This technique is commercialized by the firm corpus.e AG, Stuttgart, under the tradename "The MagicalSkin Scanner®" (see www.corpus-e.com). The inventive idea is of course not restricted to this special technology of 3D digitization based on photogrammetry, but is likewise applicable to 3D digitizers operating by the strip projection method, by the laser triangulation method, by the silhouette cut method or by other methods of 3D digitization known to those skilled in the art.

Figure 1:
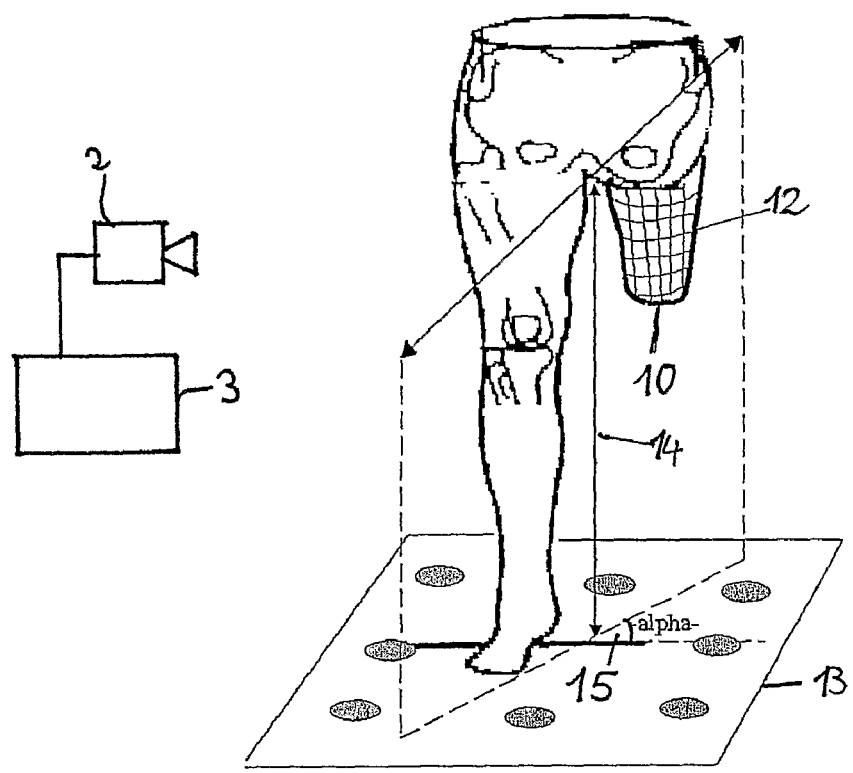
FIG. 1 shows a front view of the optically non-visible region of the ramus in the case of a patient requiring an above-knee prosthesis.

FIG. 1 shows an only partly represented patient and a schematically indicated 3D digitizer 2 with attached computer 3.

As shown in FIG. 1, the stump 10 of the patient standing upright on a photogrammetrically marked base plate 13 is clothed with an elastic cover 12 provided with marks to be evaluated by photogrammetry. The marks are only indicated by way of example; they can consist of differently coded patterns which are known to the expert of photogrammetry. In DE 101 13 211.5 of the inventor Robert Massen, various photogrammetric marking systems suitable for an automatic evaluation are described, which can be used both for marking the base plate and for marking the elastic cover. The patient is standing on the plate 13 provided with photogrammetric marks, which defines the world coordinate system and at the same time represents an absolute scale which is required for obtaining absolute XYZ coordinates. When recording the marked stump by a number of pictures taken all around by a digital camera in accordance with this technology, the region between the two thighs remains non-visible. Therefore, no 3D data can be obtained from this body region.

There is in particular missing the vertical coordinate 14 of the ramus bone in the perineal region and the ramus angle alpha 15, at which the prosthesis shaft rests on the bone and absorbs a significant part of the body weight, when the prosthesis is worn later on.

Figure 2:
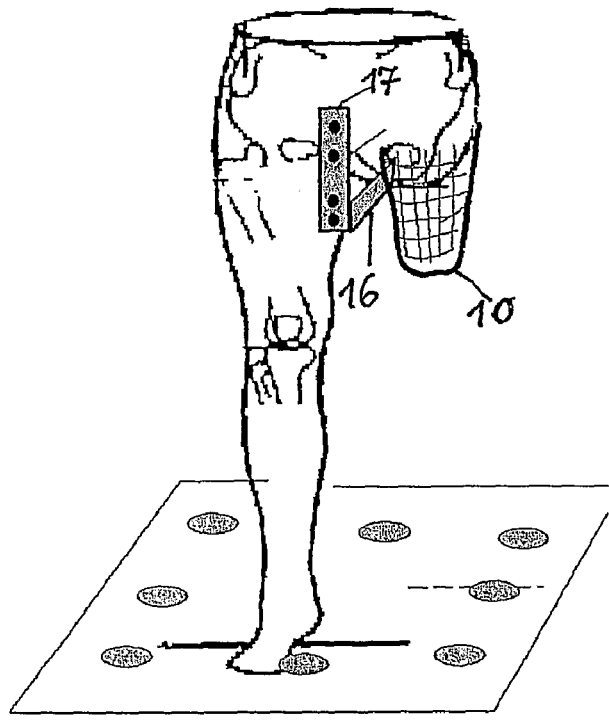
FIG. 2 shows a rigid measurement aid protruding from the ramus into the visible part of the measurement space, this part being provided with marks to be evaluated by photogrammetry.

In accordance with the invention as shown in FIG. 2, an oblong measurement aid 16 bent upwards is attached to the inside of the above-knee stump 10 and in physical contact with the ramus at the level of the perineum such that it protrudes from the non-visible region into the visible outer zone in the direction of the ramus angle. By means of the bend it is achieved that the visible, marked end 17 of the measurement aid is in a spatial position which does not cover any of the body regions to be digitized, in the present example the lower abdomen. Attachment to the elastic cover can for instance be effected by means of a Velcro seal.

During digitization, the freely visible end of the measurement aid is detected simultaneously with the visible body regions, and the precise spatial position of the marks both of the measurement aid and of the visible body parts is determined. As the aid is rigid, the required partial spatial information such as height and angular position of the ramus bone can be concluded from the XYZ coordinates of these marks. Although there are not provided any complete XYZ data of the non-visible body region, there is provided a partial spatial information such as height, angular direction etc., which for the proper manufacture of the shaft completes the missing points in the 3D model obtained by the 3D digitizer.

By mounting the measurement aid under pressure on the ramus bone in accordance with the invention, it is achieved at the same time that spatial coordinates are obtained for an anatomical part located under the adipose tissue and hence could principally not be determined from the marked cover lying on the adipose tissue, even if this region was visible.

Figure 3:
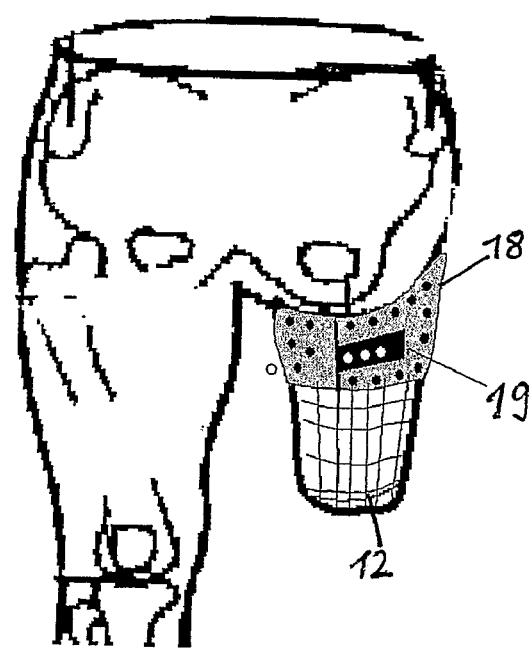
FIG. 3 shows a measurement aid in the form of an adjustable ring, which on the visible surface is provided with marks to be evaluated by photogrammetry and has a likewise marked belt for determining the circumference at the non-visible points of the thigh.

In another exemplary embodiment of the invention as shown in FIG. 3, a photogrammetrically marked auxiliary ring 18 of adjustable circumference is moved as measurement aid over the marked cover 12 into the position of the final shaft connection and is aligned there with the ramus angle. By adjusting the diameter by means of a likewise marked belt construction 19, the auxiliary ring is adapted to the thigh width.

The marks on the surface serve to determine the spatial coordinates and thus the spatial position of the auxiliary ring with respect to the world coordinate system and hence indirectly also with respect to the marked above-knee stump. Since the 3D model of the marked auxiliary ring is known from its CAD construction and by means of the position of the belt marks its diameter individually adapted to the thigh can be determined by the 3D digitizer, the 3D model of the auxiliary ring 18 stored in a CAD computer can easily be converted to the individual diameter of the patient. Since the spatial position of the auxiliary ring 18 with respect to the digitized stump 10 is known at the same time, all the necessary 3D information is available for automatically fabricating an individual prosthesis shaft starting with the stump end and reaching up to the ramus.

It is another inventive idea to make the marked auxiliary ring from semiplastic, photogrammetrically marked material. This material is molded onto the thigh by the orthopaedist like soft gypsum, and after the manual deformation at least briefly maintains its spatial shape for the duration of the digitization. At least for the visible part of the thigh, the 3D digitizer thus determines that spatial shape which a final shaft compressing the adipose tissue should take. The non-visible part is determined for instance as described above by means of a measurement aid protruding into the visible measurement space, which expediently is attached to the auxiliary ring and protrudes into the visible measurement space for instance under the ramus angle.

In accordance with another idea of the invention, the measurement means is mounted under a load, i.e. loaded by the non-visible body parts. In the case of a vertical load, this can for instance be effected in that the measurement means is supported by means of a support facing the base plate on which the patient stands during the 3D digitization. In the case of a radial load, for instance by the deliberate compression of the thigh by means of an annular measurement aid, the absorption of the load is achieved by the belt mounted for adjusting the diameter. In both examples it is achieved that the desired spatial coordinates under body load, i.e. like during the future wearing of the prosthesis, can be determined by means of the 3D digitizer and thus provide a much more accurate description of the spatial shape required for the production of the fitted prosthesis part than in the case of the digitization of an unloaded stump.

Figure 4:
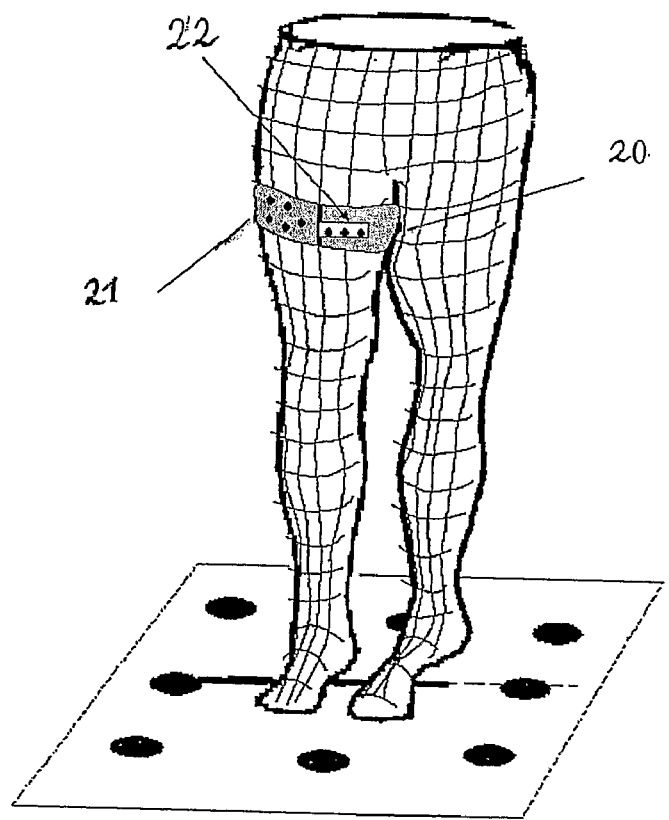
FIG. 4 shows a patient to be provided with compression stockings, where the thigh region is not visible and where the circumferential dimension in the non-visible thigh region is determined by means of a 3D scanner via a marked belt.

As a second example for explaining the inventive idea, the production of custom-fit compression stockings or compression tights for obese patients will be discussed. By way of example, we likewise assume that the "MagicalSkin Scanner®" technology is used for 3D digitization. As shown in FIG. 4, the region between the thighs 20 no longer is visible in such patients. For the custom-making or size selection of fitting compression stockings, the circumference of the legs must be known at different levels. Since the cross-sectional shape of a leg by no means is circular or elliptical, the precise circumferential dimensions can only inaccurately be determined from an only incomplete 3D model.

In accordance with the invention, at least one marked, non-stretchable belt 21 is used for this application, which belt is wound around the thigh in the non-visible region. From the position of the belt marks 22 both the spatial position and the circumference can be determined by means of the 3D digitizer. There is thus provided an important circumferential dimension, which cannot be derived precisely from the 3D model incomplete in the thigh region.

These three examples should not be construed as limiting. The inventive idea covers all possible technologies of 3D digitization, all possible bodies and body parts to be digitized both of living beings and of the inanimate nature as well as all possible marked aids which are suitable for transferring spatial information from the non-visible body regions into the measurement space visible for a 3D digitizer and which are detected simultaneously with the spatial shape of the visible body parts.

The marks on the aid can consist both of absolutely or relatively coded marks, color-coded marks, marks coded via specific background colors or marks coded by a specific mutual arrangement. In the case of 3D digitizers projecting patterns, such as strip projection digitizers or laser triangulation digitizers, the application of photogrammetrically coded marks onto the aid can be omitted and special molded parts of the aid, such as the edge thereof, can be used as a spatial mark. The aid should, however, have a sufficient optical reflection, so that these projected marks can be evaluated by the optical 3D digitizer. The end freely protruding into the measurement space for instance represents a spatial position to be detected by the 3D digitizer, which is located in a known spatial position with respect to the part of the measurement aid fixed at the body part, and therefore constitutes a "mark" in the sense of the inventive idea. It is thus possible to calculate back from this measurable position in the measurement space to the non-measurable position of the non-visible body part.

As projecting 3D digitizers also use cameras, high-contrast marks on the visible part of the measurement aid, which are detected by the cameras, can be helpful to determine the precise spatial position of the visible part of the measurement aid in the generated 3D model, just as in the case of non-projecting photogrammetrical methods.

The invention claimed is:

1. A method for optically detecting the spatial shape of bodies and body parts with partly non-visible regions, comprising the steps of:

providing at least one 3D digitizer for optically detecting the spatial shape of bodies and body parts;

positively mounting at least one shape-retaining measurement aid to the body parts not visible for and not measurable by the 3D digitizer such that said measurement aid includes parts protruding into a measurement space visible for the 3D digitizer, wherein on at least some points of its parts located in the visible measurement space said measurement aid is provided with marks to be evaluated by the 3D digitizer, said marks being located in a known spatial position with respect to the remaining parts of the measurement aid;

said measurement aid being made of a rigid material which is fixed at the non-visible body region such that the spatial position of this non-visible body region can be calculated from the 3D digitization of the marked part of the measurement aid protruding into the measurement space;

determining the spatial position of the marks of the part of the measurement aid visible for the 3D digitizer together with the spatial shape of the remaining, visible body regions;

determining geometrical information of the non-visible body regions from the measured spatial position of the visible part of the measurement aid;

using this geometrical information for supplementing a description of the spatial shape digitized incompletely because of the non-visible regions; and determining from the spatial position of the visible part of the measurement aid detected by the 3D digitizer and the spatial position of the visible body parts detected by the 3D digitizer, the 3D shape of the body or body part.

2. The method as claimed in claim 1, wherein the rigid measurement aid has an oblong shape and is bent upwards at one end thereof.

3. The method as claimed in claim 2 wherein the rigid measurement aid is fastened by pressing onto a bone, the spatial coordinates being determined for an anatomical part which is located under adipose tissue.

4. The method as claimed in claim 1, wherein the rigid measurement aid is fastened by pressing onto a bone, the spatial coordinates being determined for an anatomical part which is located under adipose tissue.

5. The method as claimed in claim 1, wherein the marked measurement aid is cuff-like and reaches around the visible and non-visible parts of an approximately cylindrical, only partly visible body part, wherein the circumference of the measurement aid is adjusted via a marked belt such that it closely rests against the approximately cylindrical body, and the position of the marked belt is chosen such that it protrudes into the visible measurement space; and determining from the common 3D digitization of the body part, the measurement aid and the marked belt, the circumference of the body part at the point of the measurement aid.

6. The method as claimed in claim 1, wherein the marked measurement aid is a molded ring mechanically adaptable to an approximately cylindrical body part to be digitized by deformation or by changing the diameter of said ring.

7. The method as claimed in claim 6, wherein the marked molded ring is at least partly made of a semi-plastic material;

prior to 3D digitization, said marked molded ring is manually molded onto the spatial shape of the non-visible, approximately cylindrical body part to be digitized; and upon being molded said ring maintains this spatial shape at least for the duration of the 3D digitization.

8. The method as claimed in claim 1, wherein the body part to be digitized is a stump which is digitized together with the measurement aid.

9. The method as claimed in claim 1, wherein the body part to be digitized is a body part for which a custom fit compression textile is to be made, which body part is digitized together with the measurement aid.

10. The method as claimed in claim 1, wherein
the body to be digitized or the body part to be digitized is clothed with an elastic, tightly fitting cover which reveals marks to be evaluated by photogrammetry;
the part of the measurement aid which protrudes into the measurement space to be detected by the 3D digitizer reveals marks to be evaluated by photogrammetry, these marks being designed such that they can be distinguished from those of the elastic cover by the methods of image processing or photogrammetry; and
the marked measurement aid is digitized photogrammetrically together with the visible body regions.

11. An arrangement for performing a method for the optical detection of the spatial shape of bodies and body parts with partly non-visible regions, comprising:
a rigid measurement aid with marks to be evaluated by photogrammetry, which is positively mounted on at least one of the non-visible regions of the body/body part;
an optical 3D digitizer which detects the spatial shape of the visible body regions and at least one visible part of the measurement aid;
a computer to which the spatial coordinates are provided, which the 3D digitizer determines for the visible regions of the body or body part as well as for the visible part of the measurement aid, wherein the computer determines geometrical information of the non-visible body regions from the stored spatial shape of the measurement aid, the known position of the marks of the measurement aid with respect to the part of the measurement aid fixed at the non-visible body part, and from the spatial position of the visible parts of the digitized body or body part, and uses this geometrical information for completing the spatial shape digitized incompletely because of the non-visible regions.

* * * * *